United States Patent
Harrington et al.

(10) Patent No.: US 8,602,030 B2
(45) Date of Patent: Dec. 10, 2013

(54) TRACHEAL TUBES WITH IMPROVED SECRETION REMOVAL SYSTEMS

(75) Inventors: Roger Harrington, Athlone (IE); Olaf Lally, Galway (IE)

(73) Assignee: Covidien LP, Mansfield, MA (US)

( * ) Notice: Subject to any disclaimer, the term of this patent is extended or adjusted under 35 U.S.C. 154(b) by 367 days.

(21) Appl. No.: 12/827,887

(22) Filed: Jun. 30, 2010

(65) Prior Publication Data

US 2012/0000471 A1  Jan. 5, 2012

(51) Int. Cl.
*A62B 9/00* (2006.01)

(52) U.S. Cl.
USPC ...................................... 128/207.14

(58) Field of Classification Search
USPC ............ 128/200.24, 207.14–207.18; 604/540–544; 606/108
See application file for complete search history.

(56) References Cited

U.S. PATENT DOCUMENTS

| | | | |
|---|---|---|---|
| 3,407,817 A * | 10/1968 | Galleher, Jr. | 128/207.15 |
| 3,964,488 A | 6/1976 | Ring et al. | |
| 4,150,676 A * | 4/1979 | Jackson | 128/207.18 |
| 4,156,428 A * | 5/1979 | Henkin | 128/207.15 |
| 4,488,548 A | 12/1984 | Agdanowski | |
| 4,584,998 A * | 4/1986 | McGrail | 128/207.15 |
| 4,840,173 A * | 6/1989 | Porter, III | 128/207.15 |
| 5,067,497 A | 11/1991 | Greear et al. | |
| 5,245,992 A | 9/1993 | Nye | |
| 5,311,864 A * | 5/1994 | Huerta | 128/207.15 |
| 5,333,608 A | 8/1994 | Cummins | |
| 6,796,309 B2 * | 9/2004 | Nash et al. | 128/207.14 |
| 6,849,042 B2 | 2/2005 | Christopher | |
| 6,860,264 B2 | 3/2005 | Christopher | |
| 6,918,391 B1 | 7/2005 | Moore | |
| 7,201,168 B2 * | 4/2007 | McGrail et al. | 128/207.14 |
| 7,360,540 B2 | 4/2008 | Brain et al. | |
| 7,481,222 B2 | 1/2009 | Reissmann | |
| 7,503,328 B2 | 3/2009 | Kolobow et al. | |
| 7,654,264 B2 * | 2/2010 | Clayton | 128/207.15 |
| 2002/0078962 A1 | 6/2002 | Nash et al. | |
| 2003/0136413 A1 | 7/2003 | Brain et al. | |
| 2003/0145860 A1 * | 8/2003 | Johnson | 128/207.15 |
| 2005/0229933 A1 | 10/2005 | McGrail et al. | |

(Continued)

FOREIGN PATENT DOCUMENTS

| | | |
|---|---|---|
| CA | 2 463 538 A1 | 10/2003 |
| EP | 1219317 A2 | 7/2002 |
| WO | 2007066332 A2 | 6/2007 |

OTHER PUBLICATIONS

International Search Report and Written Opinion for PCT Application No. PCT/US2011/039427 dated Sep. 9, 2011; 12 pgs.

(Continued)

*Primary Examiner* — Justine Yu
*Assistant Examiner* — Michael Tsai
(74) *Attorney, Agent, or Firm* — Fletcher Yoder PC

(57) ABSTRACT

Various embodiments of a tracheal tube having a tubular body with an open distal end and a tube wall with a variable thickness are provided. The tube wall may include a thickened section comprising a void. The tracheal tube may also include an offset ventilation lumen disposed in the tubular body and adapted to facilitate airflow to and from a patient. Embodiments of the tracheal tube may also include a suction lumen disposed in the thickened section of the tube wall and terminating in a port opening into the void for removal of secretions from the patient's trachea.

19 Claims, 6 Drawing Sheets

(56) References Cited

U.S. PATENT DOCUMENTS

| | | |
|---|---|---|
| 2008/0021386 A1 | 1/2008 | Clayton |
| 2008/0078399 A1 | 4/2008 | O'Neal et al. |
| 2008/0110468 A1 | 5/2008 | Nelson et al. |
| 2008/0283052 A1 | 11/2008 | Young |
| 2009/0013995 A1 | 1/2009 | Williams |
| 2009/0038620 A1 | 2/2009 | Efrati |
| 2009/0125002 A1* | 5/2009 | Totz ............... 604/528 |
| 2009/0229605 A1 | 9/2009 | Efrati et al. |
| 2010/0147309 A1 | 6/2010 | Cuevas et al. |

OTHER PUBLICATIONS

Dragoumanis, Investigating the Failure to Aspirate Subglottic Secretions with the Evac Endotracheal Tube, Anesthesia & Analgesia, Oct. 2007, vol. 105, No. 4.

* cited by examiner

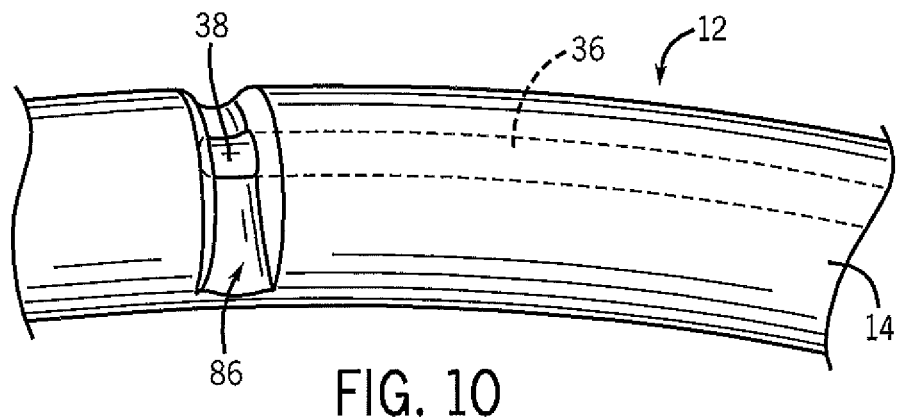
FIG. 10
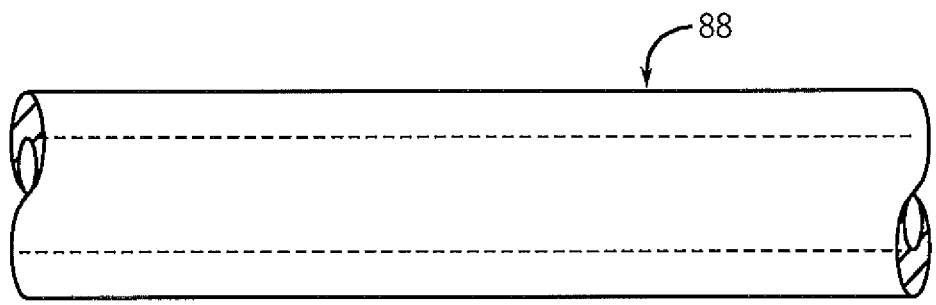
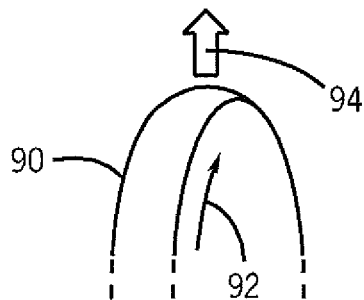
FIG. 11
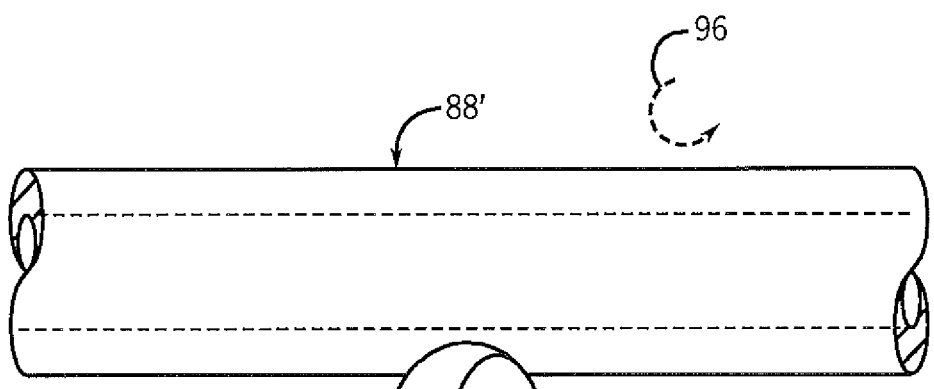
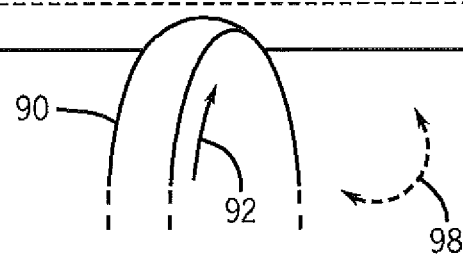
FIG. 12

TRACHEAL TUBES WITH IMPROVED SECRETION REMOVAL SYSTEMS

BACKGROUND

The present disclosure relates generally to medical devices and, more particularly, to airway devices, such as tracheal tubes.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Tracheal tubes are often placed in the airway of a patient in medical situations that necessitate protection of the airway from possible obstruction or occlusion, or to assist in respiration. For instance, tracheal tubes may be used in emergency situations, such as when a patient experiences cardiac or respiratory arrest. Such intubations increase a patient's risk of developing ventilator-associated pneumonia (VAP) due to bacterial colonization of the lower respiratory airways. In healthy individuals, mucociliary clearance removes particles and microorganisms, which helps prevent respiratory infection. However, depending upon the medical condition of the patient, clearance mechanisms may become compromised due to tracheal tube cuff inflation, and mucus accumulates at the distal end of the tracheal tube below the cuff. In many instances, such patients may remain intubated for extensive periods of time, during which mucus accumulated at the near of the cuff may drop to the proximal trachea and ultimately infect the lungs.

In many instances, it may be desirable to manage the accumulation of mucus secretions around the cuff via removal through external suctioning, administration of antibiotics, or a combination thereof. Accordingly, tracheal tubes including a suction lumen terminating in a port have been developed to target mucus secretions accumulated in the area above the cuff. Unfortunately, a curvature provided in many tracheal tubes, sometimes referred to as the "Magill curve" may force the tube toward the patient's tracheal wall and, during secretion removal, the tracheal mucosa may be sucked into the port. In such instances, the patient's mucosa may be affected and further suctioning of the accumulated secretions may be prevented or counterindicated. Accordingly, there exists a need for improved tracheal tubes with provisions that prevent or reduce the risk of such inadvertent consequences.

BRIEF DESCRIPTION OF THE DRAWINGS

Advantages of the disclosed techniques may become apparent upon reading the following detailed description and upon reference to the drawings in which:

FIG. 10 is a perspective view of an exemplary tracheal tube including a recess disposed about a portion of the circumference of the tracheal tube surrounding a suction port in accordance with aspects of the present disclosure;

FIG. 11 illustrates a first step of an exemplary method of forming the tracheal tube of FIG. 10 in accordance with aspects of the present disclosure;

FIG. 12 illustrates a second step of an exemplary method of forming the tracheal tube of FIG. 10 in accordance with aspects of the present disclosure;

DETAILED DESCRIPTION OF SPECIFIC EMBODIMENTS

Figure 1:
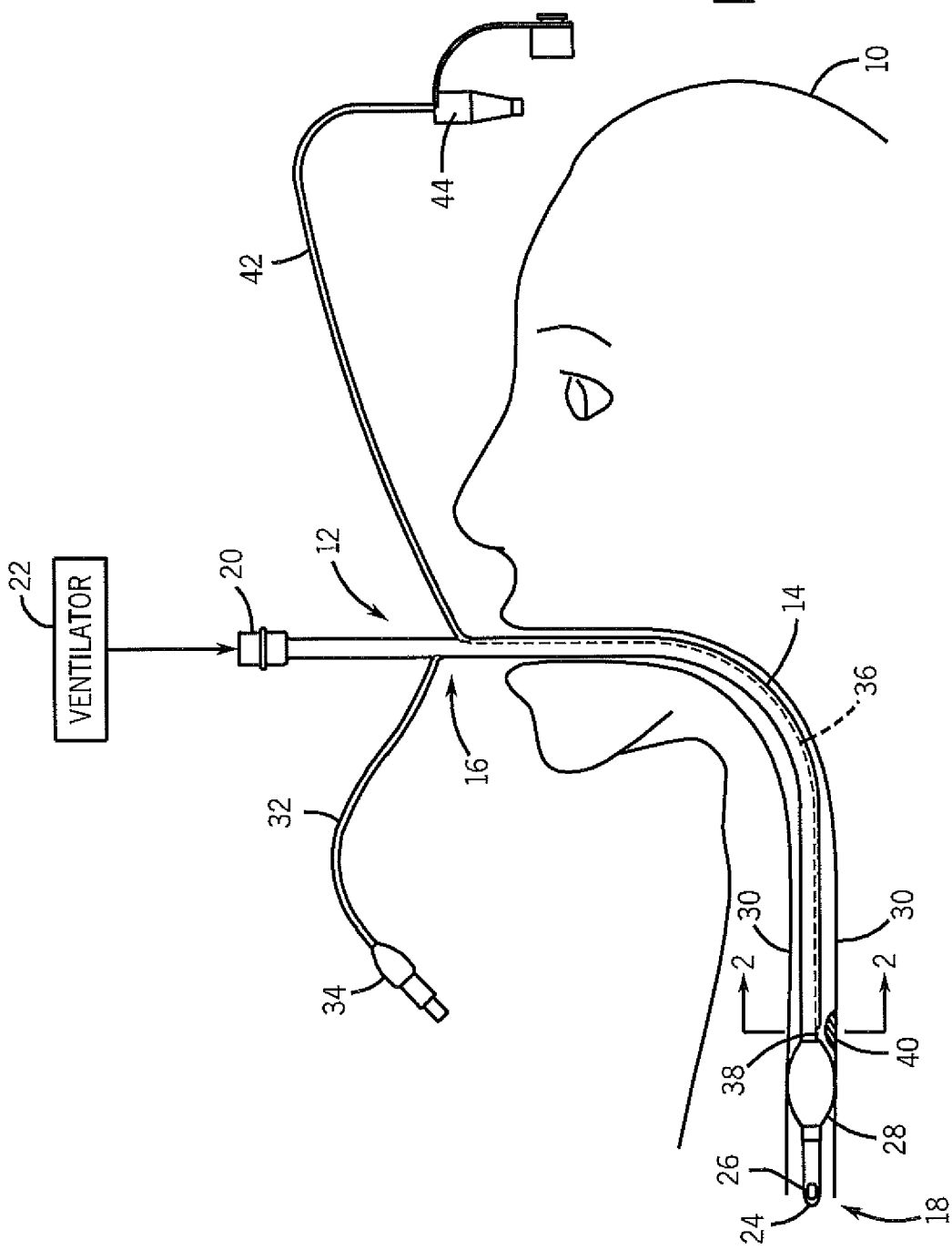
FIG. 1 illustrates an exemplary system including a patient intubated with an exemplary tracheal tube in accordance with aspects of the present disclosure.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described in detail below, embodiments of an endotracheal tube (ETT) are provided having one or more innovations that substantially prevent or eliminate suctioning of tracheal mucosa into a provided suction lumen and subsequent occlusion of an associated port. The provided tracheal tubes include at least one suction lumen terminating in a port, and may also include one or more of an offset ventilation lumen, a void or recess disposed between two lobes, duel offset ventilation lumens, a partially blocked notch port, and a localized recess surrounding the port. In some embodiments, a tracheal tube wall with a variable thickness may include a wall portion of increased thickness, which may facilitate the incorporation of one or more enlarged suction lumens terminating in one or more notch or breakout ports adapted to suction secretions from a patient's trachea.

The disclosed ETT may be disposable rather than reusable, capable of conveying gas to and from the patient, and capable of removing accumulated secretions from the patient's trachea without substantial impairment to the patient's trachea due to inadvertent suctioning. The foregoing features of the tracheal tubes described herein may offer distinct advantages over traditional tracheal tubes. For instance, traditional tracheal tubes may enable suctioning of secretions from the patient's airway without provisions for preventing occlusion of the suction port due to the inadvertent suctioning of the trachea mucosa. For further example, currently disclosed innovations, such as tracheal tube walls with variable thicknesses, may also endow the tracheal tubes with further advantages, such as improved structural integrity.

It should be noted that the provided tracheal tubes and methods of operating the tracheal tubes may be used in conjunction with auxiliary devices, such as airway accessories, ventilators, humidifiers, and so forth, which may cooperate with the tracheal tubes to maintain airflow to and from the lungs of the patient. For instance, the tracheal tubes may be placed in the trachea and coupled to a ventilator to protect the airway from possible obstruction or occlusion in emergency situations, such as when a patient experiences cardiac or respiratory arrest. That is, embodiments of the presently disclosed tracheal tubes may be utilized when ventilation with a traditional mask may be unfeasible and/or ineffective, thus necessitating use of a tracheal tube. For example, when a patient experiences a coma or areflexia, the ability of the patient to breathe without assistance may be compromised, and a tracheal tube may be inserted for ventilation purposes.

Furthermore, although the embodiments of the present invention illustrated and described herein are discussed in the context of endotracheal tubes, it should be noted that embodiments of the present invention may be applied to any of a variety of suitable airway devices. For example, the presently disclosed innovations may be associated with a tracheostomy tube, a Broncho-Cath™ tube, a specialty tube, or any other airway device with a main ventilation lumen defined by a tubular wall. Furthermore, as used herein, the term "tracheal tube" may include an endotracheal tube, a tracheostomy tube, a Broncho-Cath™ tube, a specialty tube, or any other suitable airway device.

Turning now to the drawings, FIG. 1 illustrates an exemplary system in use with a patient 10 intubated with an endotracheal tube 12 in accordance with aspects of the present disclosure. The endotracheal tube 12 includes a central tubular body 14 with proximal and distal ends 16 and 18, respectively. In the illustrated embodiment, the proximal end 16 is outfitted with a connector 20 that may be attached to a mechanical ventilator 22 during operation. The distal end 18 terminates in an opening 24 and may be placed in a patient's trachea during operation to maintain airflow to and from the patient's lungs. A Murphy's eye 26 may be located on the tubular body 14 opposite the opening 24 to prevent airway occlusion in the event the endotracheal tube 12 is improperly placed within the trachea of the patient.

As illustrated, a cuff 28, which may be inflated to seal against the walls 30 of a body cavity (e.g., a trachea), may be attached to the distal end 18 of the tubular body 14. The cuff 28 may be inflated via an inflation lumen 32 terminating in a fixture 34 located at the proximal end 16 of the tubular body 14. The tubular body 14 and the cuff 28 may be formed from materials having desirable mechanical properties (e.g., puncture resistance, pin hole resistance, tensile strength, and so forth) and desirable chemical properties (e.g., biocompatibility). In one embodiment, the walls of the cuff 28 may be made of a polyurethane (e.g., Dow Pellethane® 2363-80A) having suitable mechanical and chemical properties. In other embodiments, the walls of the cuff 28 may be made of a suitable polyvinyl chloride (PVC). In certain embodiments, the cuff 28 may be generally sized and shaped as a high volume, low pressure cuff that may be designed to be inflated to pressures between about 15 cm $H_2O$ and 30 cm $H_2O$.

The tubular body 14 may also include a suction lumen 36 that extends from a location on the endotracheal tube 12 positioned outside the body when in use to a location around the cuff 28 inside the body. The suction lumen 36 may terminate in a port 38 through which accumulated secretions 40 may be aspirated. An exterior suction tube 42 connects to the suction lumen 36 for the removal of suctioned fluids. The suction tube 42 terminates outside the body in a fixture 44 that allows the suction tube 42 to be connected to auxiliary equipment (e.g., a vacuum source) during suctioning.

In the illustrated embodiment, the single port 38 is located directly above the cuff 28 for suctioning of the secretions 40. However, in other embodiments, one or more ports may be located anywhere along the length of the tubular body 14 for aspiration of secretions from the airway of the patient 10. Furthermore, any of a variety of suitable types of ports, such as notched ports and breakout ports, may be integrated with the tracheal tube 12 for suctioning of the secretions 40. Still further, as discussed in detail below, a variety of modifications may be made to the tracheal tube body 14 to reduce or eliminate the possibility of the tracheal mucosa 30 being suctioned into the port 38. For example, in some embodiments, a void of recess may be provided in the tubular body 14 of the tracheal tube 12 in the region surrounding the port 38 to allow for suctioning of the secretions 40 from an area removed from the walls 30 of the patient's trachea. For further example, in some embodiments, a wall of the tracheal tube may include a region of increased thickness to accommodate a variety of advantageous modifications to the tracheal tube body 14. Accordingly, during use, embodiments of the present invention may have the effect of reducing or eliminating the potential to adversely affect the tracheal walls 30 and occlusion of the port 38 during suctioning of the secretions 40 from the patient's airway.

Figure 2:
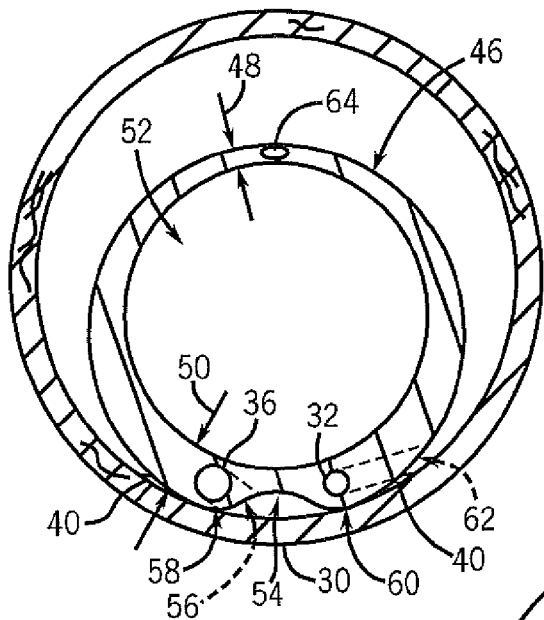
FIG. 2 is a cross sectional view of an exemplary tracheal tube taken along line 2-2 of FIG. 1, illustrating an embodiment of the tubular body including an offset ventilation lumen, a void, and a breakout port for suctioning in the void in accordance with aspects of the present disclosure.

FIG. 2 is a cross sectional view of the tracheal tube 12 taken along line 2-2 of FIG. 1, illustrating an embodiment of the tubular body 14 in the region above the cuff 28 that includes modifications that may reduce or eliminate the possibility of suctioning the tracheal mucosa 30 during use. In the illustrated embodiment, a tracheal tube wall 46 includes a variable thickness around the circumference of the tubular body 14. That is, a first thickness 48 of a first side of the tracheal tube wall 46 is substantially smaller than a second thickness 50 of a second side of the tracheal tube wall. Such a variable thickness tracheal tube wall 46 may provide for an offset ventilation lumen 52 as compared to traditional tracheal tubes, which typically include a uniform wall thickness. The tracheal tube wall 46 may be sized in such a way to accommodate the suction lumen 36 in the second side of the wall with the second thickness 50. The foregoing feature may offer distinct advantages over designs in which the tube wall 46 is of uniform thickness around the entire circumference. For example, as shown in the illustrated embodiment, the suction lumen 36 and the inflation lumen 32 may be placed at a radial position corresponding to the area of increased wall thickness, which may provide better structural integrity of the tubular body 14 as compared to traditional non-offset tracheal tubes.

In the embodiment illustrated in FIG. 2, the second side of the tracheal tube wall 46 may also include a void or recess 54 disposed in the increased wall thickness 50 and a breakout port 56 that opens into the void 54. During use, a first lobe 58 and a second lobe 60 contact the tracheal wall 30, thus providing support of the tracheal tube 12 against the tracheal mucosa and forming the void 54 to facilitate secretion removal. During operation, a vacuum is applied to the suction lumen 36 and the secretions 40 are suctioned into the suction lumen 36 via the breakout port 56. Since the breakout port 56 opens to the void 54, secretions 40 may be suctioned from the patient's trachea without undesirable suctioning of the tracheal mucosa and occlusion of the suction lumen 36. That is, the lobes 58 and 60 support the tracheal tube 12 against the tracheal wall 30 and prevent the breakout port 56 from reaching the tracheal mucosa during suctioning.

In the illustrated embodiment, the increased thickness 50 portion of the tracheal tube wall 46 also includes the inflation lumen 32 with a breakout port 62 that opens into the cuff 28. As such, the increased thickness of the second side of the tracheal tube wall 46 may be configured to support both the suction lumen 36 as well as the inflation lumen 32. Still further, the tracheal tube wall 46 may also include an X-ray lumen 64 disposed in the first side of the wall 46 with the thickness 48, such as to allow an operator to monitor the positioning of the tracheal tube 12 within the patient's trachea during insertion, intubation, or removal of the tracheal tube 12.

Figure 3:
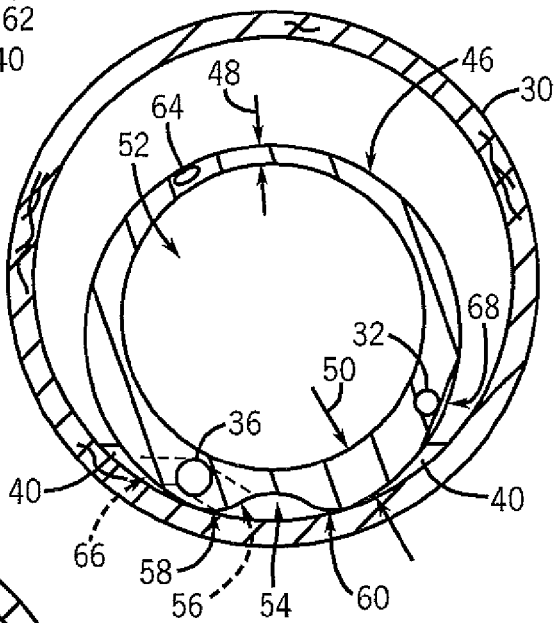
FIG. 3 is a cross sectional view of an exemplary tracheal tube including an offset ventilation lumen, a void, and a breakout port for suctioning in and around the void in accordance with aspects of the present disclosure.

FIG. 3 is a cross sectional view of an embodiment of the tracheal tube 12 of FIG. 1 including the tubular body 14 with the void 54 and the suction lumen 36 terminating in the first breakout port 56 and a second breakout port 66. That is, in the illustrated embodiment, the tube wall 46 includes an increased wall thickness 50 that accommodates the suction lumen 36 and the breakout ports 56 and 66 in the area of the void 54. As such, the illustrated embodiment provides for suctioning of the secretions 40 from the area enclosed by the void 54 via the breakout port 56 as well as from a side area adjacent the first lobe 58 via breakout port 66. During operation, the first lobe 58 and the second lobe 60 may substantially prevent suction of the tracheal mucosal wall 30 and subsequent blockage of the suction lumen 36. For example, by supporting the tracheal tube 12 such that the ports 56 and 66 are maintained in a position away from the mucosa but in the general area of the secretions 40, the lobes 58 and 60 may facilitate removal of the secretions 40 without occlusion of the lumen 36.

The illustrated tracheal tube wall 46 also includes the inflation lumen 32 terminating in a notched port 68 for inflation of the cuff 28 after patient intubation. The tracheal tube wall 46 also includes the X-ray lumen 64 that may be utilized by an operator to monitor tracheal tube placement during intubation or extubation of the patient. It should be noted that the X-ray lumen 64 may be located at any suitable radial position around the circumference of the tube wall 46.

Figure 4:
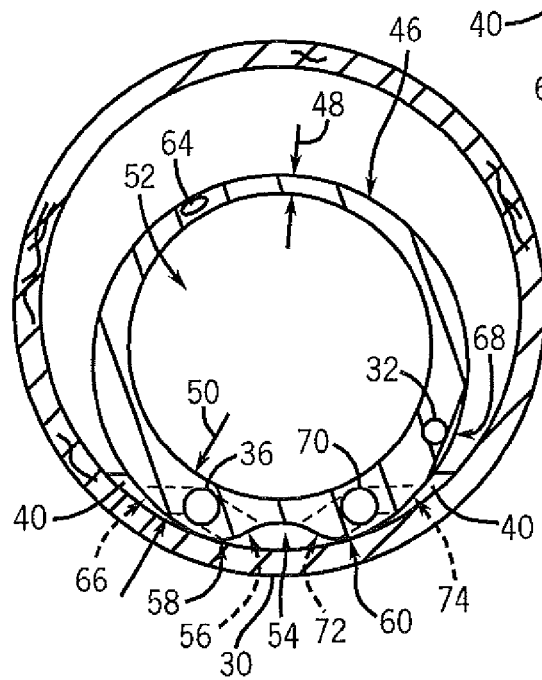
FIG. 4 is a cross sectional view of an exemplary tracheal tube including an offset ventilation lumen, a void, and two breakout ports for suctioning in and around the void in accordance with aspects of the present disclosure.

FIG. 4 is a cross sectional view of a further embodiment of the tracheal tube 12 of FIG. 3 including the tube wall 46 with the first suction lumen 36 as well as a second suction lumen 70 disposed in a portion of the tube wall 46 with increased wall thickness 50. The second suction lumen 70 is disposed adjacent the second lobe 60 opposite from the first suction lumen 36. As before, the first suction lumen terminates in the first breakout port 56 and the second breakout port 66. Similarly, the second suction lumen 70 terminates in a third breakout port 72 and a fourth breakout port 74, which are accommodated by the increased wall thickness 50 of the tube wall 46 in the area of the void 54.

During operation, secretions 40 from the area enclosed by the void 54 may be suctioned through the first suction lumen 36 via the first breakout port 56 and through the second suction lumen 70 via the third breakout port 72. Secretions 40 may also be suctioned from a first side area adjacent the first lobe 58 via breakout port 66 and a second side area adjacent the second lobe 60 via breakout port 74. As such, the first suction lumen 36 and the second suction lumen 70 may cooperate to remove the secretions 40 from the patient's trachea. Accordingly, in some embodiments, a variety of control schemes may be utilized in conjunction with one or more vacuum sources to control suctioning of the secretions 40 via the suction lumen 36 and 70 with ports 56, 66, 72, and 74.

For example, during use, a first suction device may be connected to the first suction lumen 36 and a second suction device may be connected to the second suction lumen 70 for aspiration of secretions from the airway of the patient. A controller may be connected to the suction devices to control the timing of secretion removal, to correlate secretion removal with patient expiration, to alternate suctioning between the two suction lumens, and so forth. For instance, vacuum may be applied such that mucus flow through the first suction lumen 36 and the second suction lumen 70 is established in the same direction and at the same time as airflow out of the patient during expiration. To facilitate such functions, the controller may include memory, which may be volatile or non-volatile memory, such as ROM, RAM, magnetic storage memory, optical storage memory, or a combination thereof. Furthermore, a variety of control parameters may be stored in the memory along with code configured to provide a specific output (e.g., apply vacuum every 10 seconds, alternate between the lumens, and so forth) during operation.

Figure 5:
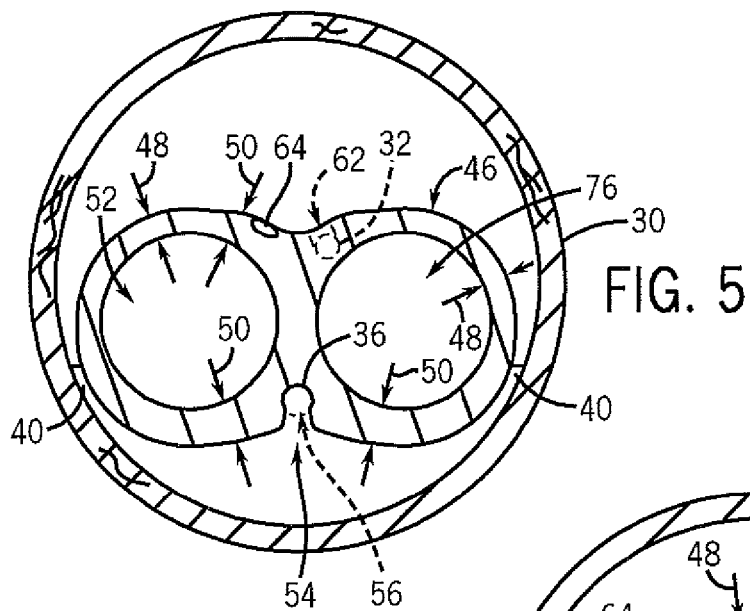
FIG. 5 is a cross sectional view of an exemplary tracheal tube including dual offset ventilation lumens, a void, and a breakout port for suctioning in the void in accordance with aspects of the present disclosure.

FIG. 5 is a cross sectional view of a further embodiment of the tracheal tube 12 of FIG. 3 including a tubular body 14 that accommodates the first ventilation lumen 52, a second ventilation lumen 76, and the suction lumen 36 disposed in an area of increased wall thickness 50. As shown, the ventilation lumens 52 and 76 are offset, thereby accommodating the suction lumen 36 terminating in the breakout port 56 in a first area of increased wall thickness 50. Also, the offset ventilation lumens 52 and 76 may accommodate the X-ray lumen 64 and the inflation lumen 32 terminating in the breakout port 62 in a second area of increased wall thickness 50. As such, if desired, the X-ray lumen 64, the inflation lumen 32, the suction lumen 36, or any combination thereof, may be enlarged as compared to traditional tracheal tubes that do not include an increased wall thickness. For example, in one embodiment, the suction lumen 36 may be enlarged to facilitate the removal of secretions 40 from the area of the void 54.

As before, during use, the breakout port 56 may remove secretions 40 from the void 54 without damage to the tracheal mucosa 30 or occlusion of the port 56. Concurrently, the ventilation lumens 52 and 76 may be utilized to facilitate airflow both to and from the patient. For example, in some embodiments, the first ventilation lumen 52 may be configured to allow airflow to the patient during inspiration, and the second ventilation lumen 76 may be configured to allow airflow from the patient during expiration. Still further, the ventilation lumens 52 and 76 may be adapted to both allow airflow both to and from the patient. Indeed, the ventilation lumens may be utilized in any suitable way to ensure that airflow is maintained both to and from the patient during intubation.

Figure 6:
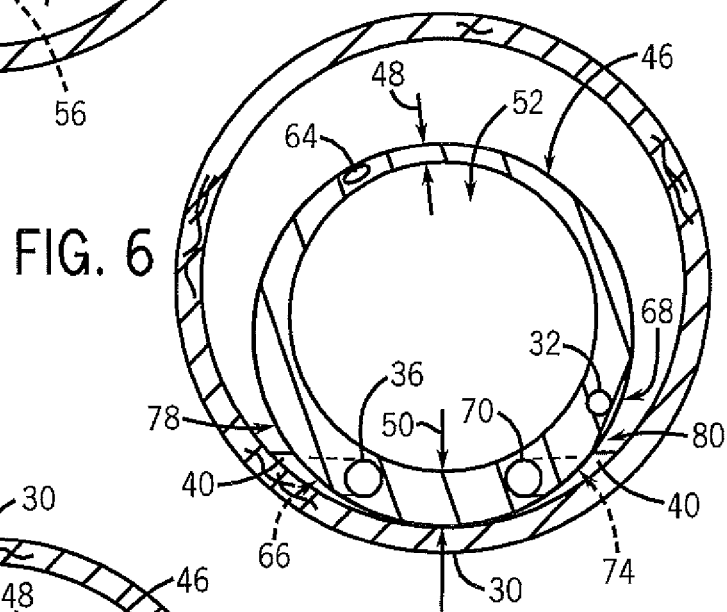
FIG. 6 is a cross sectional view of an exemplary tracheal tube including an offset ventilation lumen and two breakout ports for suctioning around the tracheal tube in accordance with aspects of the present disclosure.

FIG. 6 is a cross sectional view of a further embodiment of the tracheal tube 12 of FIG. 1 including a tube wall 46 that accommodates the first suction lumen 36 and the second suction lumen 70 in an area of increased wall thickness 50. In this embodiment, the first suction lumen 36 terminates in the breakout port 66 on a first side 78 of the tracheal tube, and the second suction lumen 70 terminates in the breakout port 74 on a second side 80 of the tracheal tube. Since the breakout ports 66 and 74 are positioned toward the first side 78 and the second side 80, the illustrated tracheal tube may allow for suctioning on either side of the tube shaft, thereby substantially preventing suctioning of the tracheal mucosa 30 during operation. As before, the illustrated tube wall 46 also includes the X-ray lumen 64 and the inflation lumen 32 terminating in the notched port 68.

During operation, the first suction lumen 36 and the second suction lumen 70 may cooperate to suction the secretions 40 from the patient's trachea. For example, a first vacuum and a second vacuum may be coupled to the first suction lumen 36 and the second suction lumen 70 and may be selectively activated to remove the secretions 40. For example, in one embodiment, the first vacuum may be adapted to apply suction to the first suction lumen 36 during a first patient expiration, and the second vacuum may be configured to apply suction to the second suction lumen 70 during a second patient expiration, and so forth, throughout the intubation period of the patient. In other embodiments, both suction lumens may be configured to remove secretions 40 simultaneously or at predetermined time intervals, which may or may not be timed with the breathing cycle of the patient.

Figure 7:
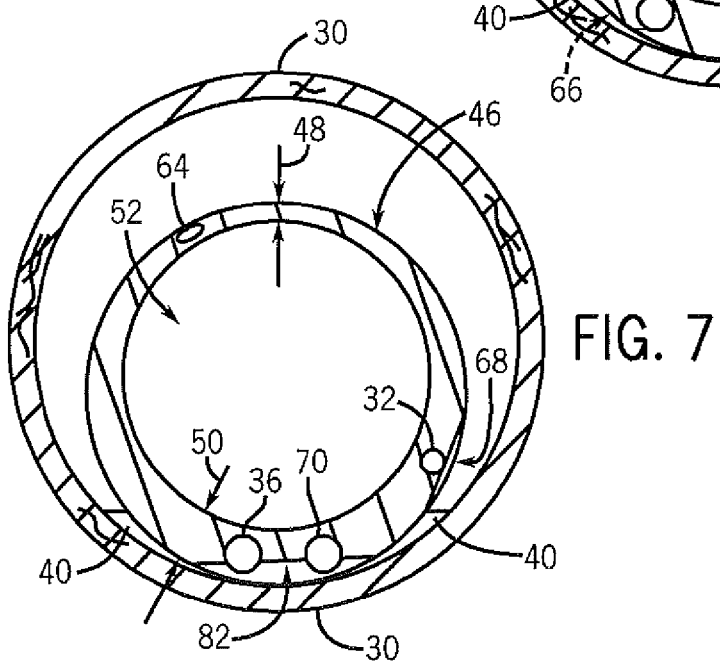
FIG. 7 is a cross sectional view of an exemplary tracheal tube including an offset ventilation lumen, two suction lumens, and a notch port for suctioning around the tracheal tube in accordance with aspects of the present disclosure.

FIG. 7 is a cross sectional view of a further embodiment of the tracheal tube 12 of FIG. 1 including a tube wall 46 that accommodates the first suction lumen 36 and the second suction lumen 70 in an area of increased wall thickness 50. In this embodiment, however, the first suction lumen 36 and the second suction lumen 70 terminate in a single enlarged notch port 82. As before, the X-ray lumen 64 and the inflation lumen 32 terminating in the notch port 68 may also be disposed in the tube wall 46. During operation, the illustrated embodiment may offer distinct advantages over traditional tracheal tubes, which do not include an offset main ventilation lumen 52. For example, since the suction lumens 36 and 70 are disposed on opposite sides of the tracheal tube shaft, suctioning through the notch port 82 may suction the secretions 40 from an area away from the tracheal mucosa 30, thus reducing or eliminating the possibility of damaging the tracheal mucosa and occluding the notch port 82 during secretion removal.

Figure 8:
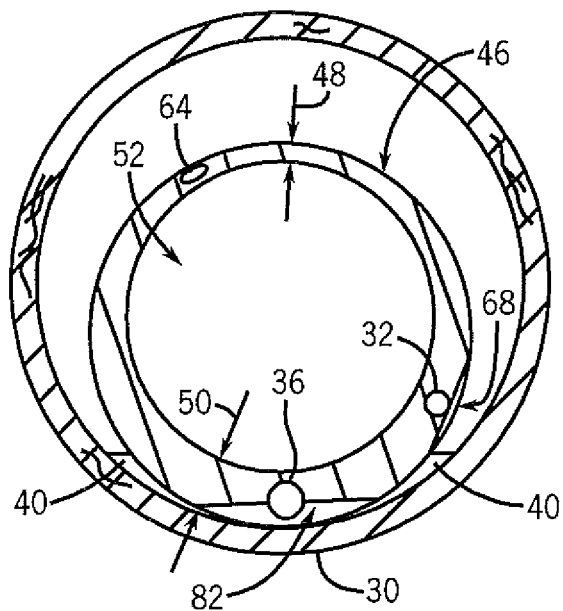
FIG. 8 is a cross sectional view of an exemplary tracheal tube including an offset ventilation lumen, a suction lumen, and a notch port for suctioning around the tracheal tube in accordance with aspects of the present disclosure.

FIG. 8 is a cross sectional view of a further embodiment of the tracheal tube 12 of FIG. 1 including a tube wall 46 that accommodates the first suction lumen 36 in an area of increased wall thickness 50. As before, the X-ray lumen 64 and the inflation lumen 32 terminating in the notch port 68 are also disposed in the tube wall 46. However, in this embodiment, the single suction lumen 36 terminates in the single notch port 82 through which secretions 40 may be suctioned. The increased wall thickness 50 may accommodate an increased suction lumen 36 provided with outlets to each side and below the tube shaft via the notch port 82. Again, such a feature may substantially reduce or eliminate the possibility of inadvertent suctioning of the tracheal mucosa and occlusion of the notch port during use.

Figure 9:
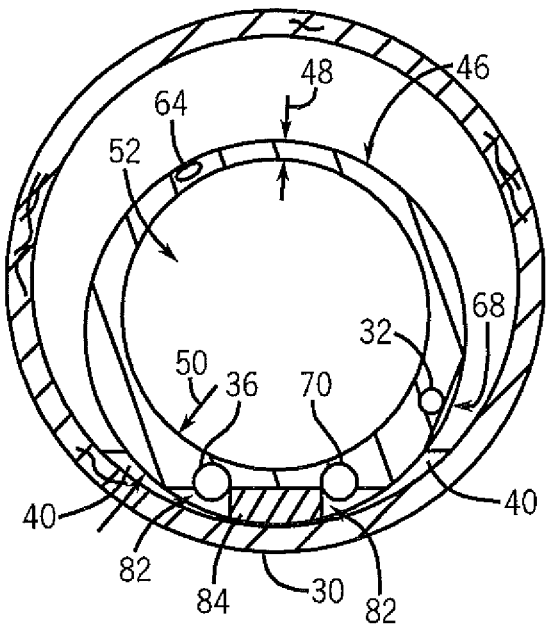
FIG. 9 is a cross sectional view of an exemplary tracheal tube including an offset ventilation lumen, two suction lumens, and a partially blocked notch port for suctioning around the tracheal tube in accordance with aspects of the present disclosure.

FIG. 9 is a cross sectional view of a further embodiment of the tracheal tube 12 of FIG. 1 including a tube wall 46 that accommodates the first suction lumen 36 and the second suction lumen 70 in an area of increased wall thickness 50. In this embodiment, however, the first suction lumen 36 and the second suction lumen 70 terminate in the single notch port 82 including a blocking member 84. As before, the X-ray lumen 64 and the inflation lumen 32 terminating in the notch port 68 may also be disposed in the tube wall 46. In some instances, during operation, the illustrated embodiment may offer distinct advantages over embodiments that do not include the blocking member 84. For example, the blocking member 84 may facilitate the suctioning of the secretions 40 from areas disposed on opposite sides of the tracheal tube shaft, thus facilitating suctioning from areas disposed away from the tracheal mucosa 30. Again, such a feature may reduce or eliminate the possibility of damaging the tracheal mucosa and occluding the notch port 82 during secretion removal.

FIG. 10 is a perspective view illustrating an embodiment of the tracheal tube 12 of FIG. 1 in more detail. In this embodiment, the tubular body 14 includes a recess or void 86 disposed about a portion of the circumference of the tracheal tube 12 surrounding the port 38. For example, the recess 86 may extend between about approximately 10° and approximately 180° of the circumference of the tracheal tube 12. For further example, the recess 86 may extend between about approximately 90° and approximately 180° of the circumference of the tracheal tube 12. As illustrated, the recess 86 is localized to the area surrounding the port 38 to facilitate access of the secretions to the port 38 during operation. The foregoing feature may facilitate the accumulation of the secretions in the recess 86 and the flow of such secretions to the port 38 for removal via the suction lumen 36. The provided recess 86 may allow for the application of vacuum to the suction lumen 36 without suctioning of the tracheal mucosa since the port 38 is set back from the tracheal wall during intubation.

FIGS. 11 and 12 illustrate an exemplary method of forming the tracheal tube 12 of FIG. 10. Specifically, FIG. 11 illustrates a preformed tubular body 88 and a wheel 90 that may be rotated in a direction indicated by arrow 92 and moved toward the preformed tubular body 88, as indicated by arrow 94. FIG. 12 illustrates a tubular body 88' in contact with the rotating wheel 90 during formation of the recess 86. As shown, as the wheel 90 is rotated, the wheel 90 contacts the tubular body 88', thereby creating the localized recess 86 in the desired position along the length of the tubular body 88'. As such, a localized recess 86 may be generated in the body of the tracheal tube.

It should be noted that the wheel 90 and the tubular body 88' may each be rotated and/or moved in a variety of suitable ways such that a recess 86 of the desired size and shape may be formed in the tubular body 88'. For example, the tubular body 88' may be rotated according to arrow 96 and/or the wheel 90 may be rocked back and forth as shown by arrow 98. For further example, in some embodiments, during formation of the recess 86, the wheel 90 may be rocked back and forth such that the recess 86 may be formed in a length of the tubular body 88' greater than the width of the wheel 90. Similarly, in other embodiments, the tubular body 88' may be moved to achieve a recess 86 along a length of the tubular body 88' that is greater than the width of the wheel 90. Still further, the wheel 90 may be appropriately sized and shaped for the particular tracheal tube being formed. For example, the wheel 90 may be sized smaller for tracheal tubes designed for infant use, larger for tracheal tubes designed for adult use, and so forth.

Figure 13:
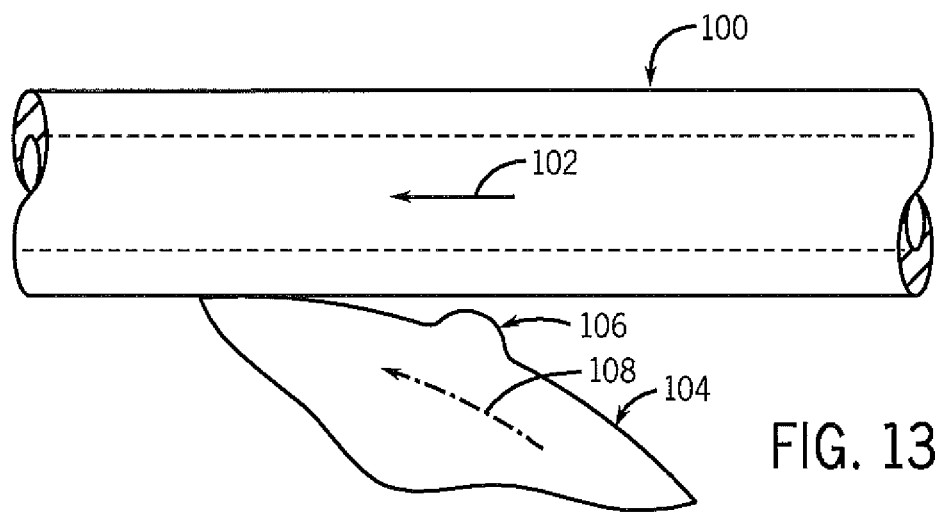
FIG. 13 illustrates a first step of an alternate exemplary method of forming the tracheal tube of FIG. 10 in accordance with aspects of the present disclosure.
Figure 14:
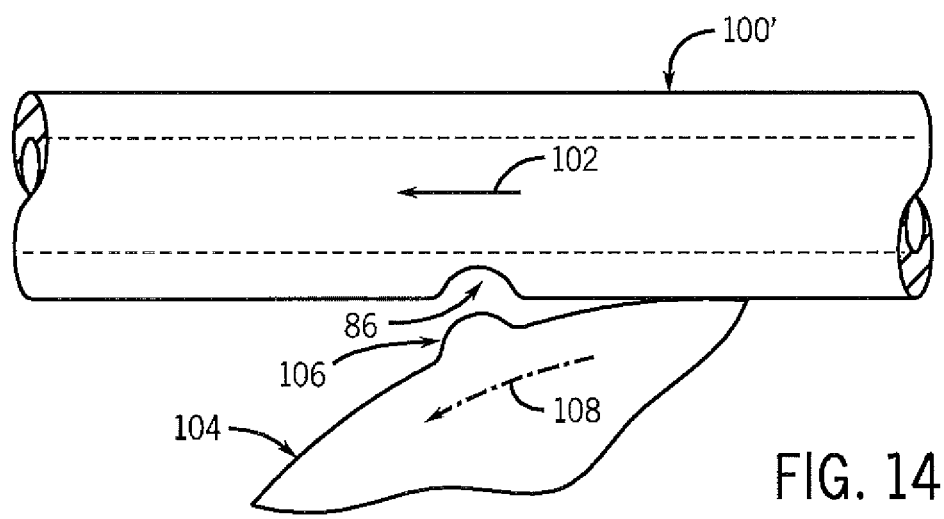
FIG. 14 illustrates a second step of an alternate exemplary method of forming the tracheal tube of FIG. 10 in accordance with aspects of the present disclosure.

FIGS. 13 and 14 illustrate an additional exemplary method of forming the tracheal tube 12 of FIG. 10. Specifically, FIG.

13 illustrates a preformed tubular body 100 that may be moved in a direction indicated by arrow 102 and a wheel 104 including a protrusion 106 that may be moved in a direction indicated by arrow 108. FIG. 14 illustrates a formed tubular body 100' being moved in direction 102 as the wheel 104 is moved in direction 108. As shown, as the wheel 104 is rotated, the protrusion 106 contacts the preformed tubular body 100, thereby creating the localized recess 86 in the desired position along the length of the formed tubular body 100'. As such, a localized recess 86 may be generated in the body of the tracheal tube. As before, it should be noted that the wheel 104 and the protrusion 106 may be appropriately sized and shaped for the particular tracheal tube being formed.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A tracheal tube, comprising:
   a tubular body comprising an open distal end and a tube wall;
   the tube wall having a first section and a thickened section;
   the thickened section comprising a first portion, a second portion and a third portion;
   the first and second portions thicker than the first section;
   the third portion thinner than the first and second portions and being disposed between the first and second portions, wherein a void is disposed in the thickened section to define the third portion;
   an offset ventilation lumen disposed in the tubular body and configured to facilitate airflow to and from a patient, and wherein the first section and the thickened section define at least a portion of the ventilation lumen; and
   a first suction lumen and a second suction lumen disposed in the thickened section of the tube wall of the tubular body, wherein both the first and second suction lumens terminate in respective first and second ports opening into the void, wherein the void is between the first and second suction lumens, and wherein secretions may be aspirated from a trachea of the patient through the first and second ports via the first and second suction lumens.

2. The tracheal tube of claim 1, wherein the first and second portions of the thickened section terminate in first and second lobes, respectively, and the void is disposed between the first and second lobes.

3. The tracheal tube of claim 1, wherein the second port is a breakout port further adapted to open into the void and to a side of the void.

4. The tracheal tube of claim 1, further comprising a cuff disposed around the tubular body and configured to be inflated to seal the cuff against a wall of the trachea of the patient.

5. The tracheal tube of claim 4, further comprising an inflation lumen disposed in the tube wall and terminating in a port, wherein the inflation lumen is configured to facilitate bidirectional airflow to and from the cuff.

6. The tracheal tube of claim 1, further comprising an X-ray lumen disposed in the tube wall and configured to allow an operator to monitor placement of the tracheal tube.

7. The tracheal tube of claim 1, further comprising a second offset ventilation lumen disposed in the tubular body and configured to facilitate airflow to and from a patient, wherein the suction lumen is disposed between the offset ventilation lumen and the second offset ventilation lumen.

8. The tracheal tube of claim 1, wherein the offset ventilation lumen is configured to be coupled to a ventilator.

9. The tracheal tube of claim 1, wherein the first suction lumen is configured to be coupled to a suctioning device.

10. The tracheal tube of claim 1, wherein the first port and the second port are positioned on opposing faces of the void.

11. A tracheal tube, comprising:
    a tubular body comprising an open distal end and a tube wall;
    the tube wall having a first wall section having a first thickness and a thickened wall section around a circumference of the tubular body, wherein the thickened wall section is thicker than the first wall section and wherein tube wall gradually and continuously increases in a direction from the first wall section to the thickened wall section, the thickened wall section having a portion configured to contact a tracheal mucosa;
    an offset ventilation lumen disposed in the tubular body and defined by the first wall section and the thickened wall section and configured to facilitate airflow to and from a patient; and
    a first suction lumen and a second suction lumen disposed in the thickened wall section of the tube wall of the tubular body, wherein both the first and second suction lumen terminates in notched ports disposed between the first and second suction lumens, wherein secretions may be aspirated from a trachea of the patient from one or more sides a shaft of the tracheal tube radially displaced from the portion of the thickened section in contact with the tracheal mucosa through the notched ports via the first and second suction lumens.

12. The tracheal tube of claim 11, wherein the first suction lumen is configured to suction from a first side of the shaft of the tracheal tube and the second suction lumen is configured to suction from a second side of the shaft of the tracheal tube.

13. The tracheal tube of claim 12, comprising a blocking member configured to block a center portion of the notched port.

14. The tracheal tube of claim 11, wherein the first suction lumen is configured to be coupled to a suctioning device.

15. A tracheal tube, comprising:
    a tubular body comprising an open distal end and a tube wall;
    the tube wall having a recess disposed about a portion of a circumference of the tubular body, the tube wall having a first wall section having and a thickened wall section around a circumference of the tubular body, wherein the thickened wall section is thicker than the first wall section and wherein the tube wall gradually and continuously increases in thickness in a direction from the first wall section to the thickened wall section;
    a ventilation lumen disposed in the tubular body and configured to facilitate airflow to and from a patient, and wherein the first section and the thickened section define at least a portion of the ventilation lumen; and
    a first suction lumen and a second suction lumen disposed in the tube wall of the tubular body terminating in ports opening into the recess, wherein the recess is between the first and second suction lumens, and wherein secretions may be aspirated from a trachea of the patient through the ports via the first and second suction lumens.

16. The tracheal tube of claim 15, wherein the recess is configured to facilitate an accumulation of secretions within the recess.

17. The tracheal tube of claim 15, wherein the recess is configured to facilitate a funneling of accumulated secretions to the port.

18. The tracheal tube of claim 15, wherein the recess extends between 10° and 180° of the circumference of the tubular body.

19. The tracheal tube of claim 15, wherein the first suction lumen is configured to be coupled to a suctioning device.

* * * * *